United States Patent
Wang et al.

(10) Patent No.: US 9,388,102 B2
(45) Date of Patent: *Jul. 12, 2016

(54) PROCESS FOR PRODUCING PHENOL

(75) Inventors: Kun Wang, Bridgewater, NJ (US);
Roberto Garcia, Easton, PA (US);
Jihad M. Dakka, Whitehouse Station, NJ (US); Edmund J. Mozeleski, Somerset, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 244 days.

This patent is subject to a terminal disclaimer.

(21) Appl. No.: 14/110,859

(22) PCT Filed: Dec. 15, 2011

(86) PCT No.: PCT/US2011/065056
§ 371 (c)(1),
(2), (4) Date: Dec. 18, 2013

(87) PCT Pub. No.: WO2012/145028
PCT Pub. Date: Oct. 26, 2012

(65) Prior Publication Data
US 2015/0307427 A1    Oct. 29, 2015

Related U.S. Application Data

(60) Provisional application No. 61/476,893, filed on Apr. 19, 2011, provisional application No. 61/502,985, filed on Jun. 30, 2011.

(51) Int. Cl.
*C07C 37/08* (2006.01)
*C07C 407/00* (2006.01)
(Continued)

(52) U.S. Cl.
CPC .............. *C07C 37/08* (2013.01); *B01J 29/06* (2013.01); *B01J 29/082* (2013.01); *B01J 29/084* (2013.01);
(Continued)

(58) Field of Classification Search
CPC ...... C07C 37/08; C07C 39/04; C07C 409/16; C07C 45/53; C07C 49/403
See application file for complete search history.

(56) References Cited

U.S. PATENT DOCUMENTS 3,821,314 A   6/1974   Arkell et al.
3,959,381 A   5/1976   Arkell et al.
(Continued)

FOREIGN PATENT DOCUMENTS

EP   0293032   11/1988
EP   0 492 807   7/1992
(Continued)

OTHER PUBLICATIONS

JP2007099745A; Published Apr. 19, 2007; pp. 1-4; English translation.*

(Continued)

*Primary Examiner* — Fereydoun G Sajjadi
*Assistant Examiner* — Medhanit Bahta
(74) *Attorney, Agent, or Firm* — Stephen A. Baehl (57) ABSTRACT

In a process for producing phenol, cyclohexylbenzene is contacted with an oxygen-containing compound in the presence of an oxidation catalyst comprising a cyclic imide under oxidation conditions effective to produce a product comprising cyclohexylbenzene hydroperoxide and unreacted cyclic imide catalyst. Without removing all the unreacted cyclic imide catalyst, at least a portion of the product is contacted with an acidic molecular sieve under conditions effective to adsorb at least a portion of the unreacted cyclic imide and to convert at least part of the cyclohexylbenzene hydroperoxide in the product portion into phenol and cyclohexanone.

22 Claims, 1 Drawing Sheet

(51) Int. Cl.

| | | |
|---|---|---|
| *C07C 409/16* | (2006.01) | |
| *C07C 45/53* | (2006.01) | |
| *C07C 2/74* | (2006.01) | |
| *C07C 39/04* | (2006.01) | |
| *C07C 49/403* | (2006.01) | |
| *B01J 29/06* | (2006.01) | |
| *B01J 29/08* | (2006.01) | |
| *C07C 37/86* | (2006.01) | |

(52) U.S. Cl.
CPC . *C07C 2/74* (2013.01); *C07C 37/86* (2013.01); *C07C 39/04* (2013.01); *C07C 45/53* (2013.01); *C07C 49/403* (2013.01); *C07C 407/00* (2013.01); *C07C 409/16* (2013.01); *C07C 2101/14* (2013.01)

(56) References Cited

U.S. PATENT DOCUMENTS

| | | | |
|---|---|---|---|
| 4,021,490 | A | 5/1977 | Hudson |
| 4,230,638 | A | 10/1980 | Murtha |
| 4,262,151 | A | 4/1981 | Pujado |
| 4,358,618 | A | 11/1982 | Sifniades et al. |
| 4,439,409 | A | 3/1984 | Puppe et al. |
| 4,480,141 | A | 10/1984 | Drake |
| 4,482,757 | A | 11/1984 | Drake |
| 4,487,970 | A | 12/1984 | Drake |
| 4,490,565 | A | 12/1984 | Chang et al. |
| 4,490,566 | A | 12/1984 | Chang et al. |
| 4,826,667 | A | 5/1989 | Zones et al. |
| 4,870,217 | A | 9/1989 | Knifton |
| 4,898,995 | A | 2/1990 | Knifton et al. |
| 4,954,325 | A | 9/1990 | Rubin et al. |
| 5,236,575 | A | 8/1993 | Bennett et al. |
| 5,250,277 | A | 10/1993 | Kresge et al. |
| 5,254,751 | A | 10/1993 | Zakoshansky |
| 5,362,697 | A | 11/1994 | Fung et al. |
| 6,014,018 | A | 1/2000 | Wu et al. |
| 6,037,513 | A | 3/2000 | Chang et al. |
| 6,049,018 | A | 4/2000 | Calabro et al. |
| 6,077,498 | A | 6/2000 | Diaz Cabañas et al. |
| 6,169,215 | B1 | 1/2001 | Levin et al. |
| 6,284,927 | B1 | 9/2001 | Druliner et al. |
| 6,720,462 | B2 | 4/2004 | Kuhnle et al. |
| 6,756,030 | B1 | 6/2004 | Rohde et al. |
| 6,852,893 | B2 | 2/2005 | Kuhnle et al. |
| 2004/0162446 | A1 | 8/2004 | Black |
| 2004/0236152 | A1 | 11/2004 | Black et al. |
| 2007/0265476 | A1 | 11/2007 | Dakka et al. |

FOREIGN PATENT DOCUMENTS

| | | |
|---|---|---|
| GB | 681613 | 11/1950 |
| JP | 2007-099745 | 4/2007 |
| JP | 2007-099746 | 4/2007 |
| WO | WO 97/17290 | 5/1997 |
| WO | 2006/015826 | 2/2006 |
| WO | 2006/027359 | 3/2006 |
| WO | 2008/128638 | 10/2008 |
| WO | WO 2009/025939 | 2/2009 |
| WO | 2009/058527 | 5/2009 |
| WO | WO 2009/131769 | 10/2009 |
| WO | WO 2010/042261 | 4/2010 |
| WO | 2010/098916 | 9/2010 |
| WO | WO 2011/001244 | 1/2011 |
| WO | 2011/031374 | 3/2011 |
| WO | 2012/145028 | 10/2012 |
| WO | 2012/145029 | 10/2012 |
| WO | 2012/145030 | 10/2012 |
| WO | 2012/145031 | 10/2012 |
| WO | WO 2012/145032 | 10/2012 |

OTHER PUBLICATIONS

FAU reference (Published Mar. 5, 2001) p. 1.*
U.S. Appl. No. 61/502,979, entitled, "*Process for Producing Phenol*", filed Jun. 30, 2011.
U.S. Appl. No. 61/538,332, entitled, "*Process for Producing Phenol*", filed Sep. 23, 2011.
U.S. Appl. No. 61/544,341, entitled "*Mixed Metal Oxide Catalysts and Use Thereof*", filed Oct. 7, 2011.
U.S. Appl. No. 61/237,983, entitled, "*Oxidation of Hydrocarbons*", filed Aug. 28, 2009.
U.S. Appl. No. 61/104,292, entitled, "*Process for Producing Phenol*", filed Oct. 10, 2008.
Koltunov et al., "*Efficient Cleavage of Cumene Hydroperoxide over HUSY zeolites: The role of Bronsted activity*", Applied Catalysis A: General, vol. 336, pp. 29-34 (2008).
Ishii et al., "*Recent progress in aerobic oxidation of hydrocarbons by N-hydroxyimides*", ScienceDirect, Catalysis Today, 117 (2006), pp. 105-113.
Meier et al., "*Framework type data FAU zeolites*", Atlas of zeolites Jan. 2001, XP55007150, Retrieved from the Internet: URL:http://izase.ethz.ch/fmi/xsl/IZA-SC/Atlas_pdf/FAU.pdf, retrieved on Sep. 14, 2011.
Aoki et al., "One-Pot Synthesis of Phenol and Cyclohexanone from Cyclohexylbenzene Catalyzed by N-Hydroxyphthalimide (NHPI)", Tetrahedron, 2005, vol. 61, pp. 5219-5222.
Knifton et al., "Phenol/Acetone Cogeneration via Solid Acid Catalysis", Applied Catalysis A: General, 1997, vol. 161, pp. 199-211.
Maksimov et al., "$WO_3/MO_2$ (M=Zr, Sn, Ti) Heterogeneous Acid Catalysts: Synthesis, Study, and Use in Cumene Hydroperoxide Decomposition", Kinetics and Catalysis, 2006, vol. 47, No. 4, pp. 564-571.
Schmidt et al., "New Developments in the Sunoco/UOP Phenol Technology", presented at the AIChE Spring Meeting, Apr. 2004, New Orleans, LA.
Selvin et al., "Catalytic Decomposition of Cumene Hydroperoxide into Phenol and Acetone", Applied Catalysis A: General, 2001, vol. 219, pp. 125-129.
Zakoshansky, "Acid-catalytic Cumene Hydroperoxide Cleavage Process in Boiling Acetone Medium", presented at the AIChE Spring Meeting, Mar. 2002, New Orleans, LA.
Ch. Baerlocher and L.B. McCusker, "Framework Type FAU", in Database of Zeolite Structures, available at http://iZasc-mirror.la.asu.edu/fmi/xsl/IZA-SC/ftc_fw.xsl?-db=Atlas_main&-lay=fw&-max=25&STC=FAU&-find (retrieved Mar. 5, 2015).

* cited by examiner

PROCESS FOR PRODUCING PHENOL

PRIORITY CLAIM TO RELATED APPLICATIONS

This application is a National Stage Application of International Application No. PCT/US2011/065056 filed Dec. 15, 2011, which claims priority to U.S. Provisional Application Ser. No. 61/476,893 filed Apr. 19, 2011 and U.S. Provisional Application Ser. No. 61/502,985 filed Jun. 30, 2011, the disclosures of which are fully incorporated herein by their reference.

CROSS REFERENCE TO RELATED PATENT APPLICATIONS

This application is related to U.S. Provisional Application Ser. No. 61/502,979 filed Jun. 30, 2011; U.S. Provisional Application Ser. No. 61/538,332 filed Sep. 23, 2011; U.S. Provisional Application Ser. No. 61/544,341 filed Oct. 7, 2011 and International Patent Cooperation Treaty Application No. PCT/US2011/065063, filed Dec. 15, 2011.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide into equimolar amounts of phenol and acetone, a co-product.

It is also known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. The '513 patent also discloses that the resultant cyclohexylbenzene can be oxidized to the corresponding hydroperoxide, which is then decomposed to the desired phenol and cyclohexanone co-product.

There are, however, a number of problems associated with producing phenol via cyclohexylbenzene rather than the cumene-based Hock process. Firstly, oxidation of cyclohexylbenzene to cyclohexylbenzene hydroperoxide is much more difficult than oxidation of cumene and requires elevated temperatures and the use of a catalyst, generally a cyclic imide, such as N-hydroxyphthalimide (NHPI), to achieve acceptable rates of conversion. Not only are cyclic imide catalysts expensive but also, unless removed from the oxidation products prior to the cleavage step, they may cause problems in downstream separation processes and affect the quality of the final products. There is therefore strong incentive to separate the cyclic imide catalyst from the oxidation effluent. In addition, the cleavage chemistry for cyclohexylbenzene hydroperoxide is more complicated than that for cumene hydroperoxide, particularly since more routes for by-product formation exist with cyclohexylbenzene hydroperoxide cleavage. Moreover, cyclohexanone is more prone to acid-catalyzed aldol condensation reactions than acetone so that significant yield loss is possible unless the cyclohexylbenzene hydroperoxide cleavage step is closely controlled.

In the conventional cumene-based Hock process, the cleavage catalyst is normally sulfuric acid. However, even for the cleavage of cumene hydroperoxide, there are significant disadvantages of using sulfuric acid as the catalyst in that 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal and the waste water needs to be treated. Therefore, there are strong incentives to replace sulfuric acid with a heterogeneous cleavage catalyst that eliminates these drawbacks.

The patent and academic literature is replete with suggestions for replacing sulfuric acid in the cleavage of cumene hydroperoxide. For example, U.S. Pat. No. 4,490,565 discloses that zeolite beta is an effective replacement for sulfuric acid in the cleavage of cumene hydroperoxide and indicates that the yields, conversions and selectivities are generally superior to those produced by the use of the large pore zeolites X and Y. In U.S. Pat. No. 4,490,566, similar improvements over the large pore zeolites X and Y are reported with intermediate pore size zeolites, such as ZSM-5. In contrast, in an article entitled "Efficient Cleavage of Cumene Hydroperoxide over HUSY zeolites: The role of Bronsted activity", *Applied Catalysis A: General*, 336 (2008), pages 29-34, Koltonov et al. report that cumene hydroperoxide readily undergoes decomposition over HUSY zeolites of high (15 to 40) Si/Al ratio with good selectivity to phenol and acetone and with efficiency even comparable to that of sulfuric acid. Despite, or possibly because of, these varying recommendations, most commercial processes for the cleavage of cumene hydroperoxide continue to use sulfuric acid as the catalyst.

Less interest has been focused on the cleavage of cyclohexylbenzene hydroperoxide, although International Patent Publication No. WO2011/001244 discloses that cyclohexylbenzene hydroperoxide can be converted to phenol and cyclohexanone in the presence of a variety of homogeneous or heterogeneous acid catalysts selected from Brønsted acids and Lewis acids. Suitable homogeneous catalysts are said to include protic acids selected from sulfuric acid, phosphoric acid, hydrochloric acid, and p-toluenesulfonic acid. Solid Brønsted acids such as Amberlyst and Lewis acids selected from ferric chloride, zinc chloride, and boron trifluoride are also disclosed. In addition, suitable heterogeneous acids are said to include zeolite beta, zeolite Y, zeolite X, ZSM-5, ZSM-12, and mordenite. However, in the process of WO2011/001244, the catalyst used in the oxidation step is removed from the oxidation effluent before the cyclohexylbenzene hydroperoxide is fed to the cleavage step.

According to the present invention, it has now been found that acidic molecular sieves, such as FAU type zeolites, are not only effective catalysts for the cleavage of cyclohexylbenzene hydroperoxide, they are also effective adsorbents for the cyclic imide catalysts employed in the oxidation reaction. Thus, by using an acidic molecular sieve as the cleavage catalyst, it is possible to remove the cyclic imide catalyst from the oxidation effluent simultaneously with the conversion of the cyclohexylbenzene hydroperoxide to phenol and cyclohexanone. In this way the need for a separate step of removing the cyclic imide catalyst from the oxidation effluent can be obviated. Once acidic molecular sieve has become saturated with the cyclic imide, the adsorption/cleavage process can be temporarily suspended to allow the cyclic imide to be desorbed from the molecular sieve for recycle to the oxidation step. After removal the cyclic imide, the regenerated molecular sieve can be returned to adsorption/cleavage duty.

SUMMARY

Accordingly, the invention resides in one aspect in a process for producing phenol, the process comprising:

(a) contacting cyclohexylbenzene with an oxygen-containing compound in the presence of an oxidation catalyst comprising a cyclic imide under oxidation conditions effective to produce a product comprising cyclohexylbenzene hydroperoxide and unreacted cyclic imide catalyst; and (b) contacting at least a portion of the product with an acidic molecular sieve under conditions effective to adsorb at least part of the unreacted cyclic imide and convert at least a portion of the cyclohexylbenzene hydroperoxide in said product into phenol and cyclohexanone, wherein less than 50 wt % of the unreacted cyclic imide catalyst is removed from the product prior to the contacting step (b).

Conveniently, the acidic molecular sieve comprises an aluminosilicate zeolite and especially an aluminosilicate zeolite has a pore size greater than 7 Å.

In one embodiment, the aluminosilicate zeolite comprises a FAU type zeolite, and especially a FAU type zeolite has a unit cell size less than 24.35 Å, such as less than or equal to 24.30 Å.

Conveniently, the conditions in step (b) include a temperature of about 20° C. to about 200° C. and a pressure of about 100 kPa to about 2000 kPa.

In one embodiment, said contacting step (b) is conducted in at least a first reactor and a second reactor connected in series. Conveniently, the first reactor is operated at a temperature of about 20° C. to about 120° C. and a pressure of about 100 kPa to about 500 kPa, and the second reactor is operated at a temperature of about 40° C. to about 180° C. and a pressure of about 100 kPa to about 1000 kPa.

In another embodiment, said contacting step (b) is conducted in at least one of a plurality of reactors connected in parallel. Conveniently, the cleavage catalyst is regenerated in a first reactor during operation of the contacting step (b) in a second reactor.

In one embodiment, said contacting step (b) is at least partly conducted in a continuous stirred tank reactor (CSTR). Conveniently, the cleavage catalyst is continuously or periodically withdrawn downstream of the contacting step (b) and regenerated. Typically, the regenerated catalyst is returned to the contacting step (b). Conveniently, the cleavage catalyst is continuously, or periodically added to the contacting step (b) to maintain conversion.

In another embodiment, said contacting step (b) is at least partly conducted in a fixed bed reactor.

In a further aspect, the invention resides in a process for producing phenol, the process comprising:

(a) contacting cyclohexylbenzene with an oxygen-containing compound in the presence of an oxidation catalyst comprising a cyclic imide under oxidation conditions effective to produce a product comprising cyclohexylbenzene hydroperoxide and cyclic imide catalyst; and (b) contacting at least a portion of the product containing cyclohexylbenzene hydroperoxide and at least 50 ppm of the cyclic imide catalyst with an acidic molecular sieve under conditions effective to adsorb at least part of the cyclic imide and to convert at least part of the cyclohexylbenzene hydroperoxide in said product portion into phenol and cyclohexanone.

Conveniently, at least part of the cyclic imide catalyst is desorbed from said acidic molecular sieve and recycled to said contacting (a).

In yet a further aspect, the invention resides in a process for producing phenol, the process comprising:

(a) hydroalkylating benzene with hydrogen in the presence of a hydroalkylation catalyst under conditions effective to produce a hydroalkylation reaction product comprising cyclohexylbenzene;

(b) separating cyclohexylbenzene from said hydroalkylation reaction product;

(c) contacting at least a portion of said cyclohexylbenzene from said separating (b) with an oxygen-containing compound in the presence of an oxidation catalyst comprising a cyclic imide under oxidation conditions effective to produce a product comprising cyclohexylbenzene hydroperoxide and unreacted cyclic imide catalyst; and (d) contacting at least a portion of the product with an acidic molecular sieve under conditions effective to adsorb at least part of the cyclic imide and to convert at least part of the cyclohexylbenzene hydroperoxide in said product portion into phenol and cyclohexanone, wherein less than 50% of the unreacted cyclic imide catalyst is removed from the product prior to the contacting step (d).

DETAILED DESCRIPTION OF THE EMBODIMENTS

Described herein is a process for producing phenol, in which cyclohexylbenzene is oxidized in the presence of a cyclic imide catalyst and then, without removing all the cyclic imide, at least a portion of the resulting cyclohexylbenzene hydroperoxide is cleaved into phenol and cyclohexanone in the presence of a molecular sieve catalyst. The use of a molecular sieve for the cleavage reaction avoids the disadvantages inherent in the use of a homogeneous cleavage catalyst, such as sulfuric acid. In addition, the molecular sieve adsorbs at least part of the cyclic imide remaining from the oxidation reaction, thereby reducing or obviating the need for a separate step to remove the oxidation catalyst from the cleavage feed.

In one preferred embodiment, the present oxidation and cleavage steps form part of an integrated process for producing phenol and cyclohexanone from benzene, in which the benzene is converted to cyclohexylbenzene, the cyclohexylbenzene is then oxidized to cyclohexylbenzene hydroperox- ide and the cyclohexylbenzene hydroperoxide is cleaved to produce phenol and cyclohexanone. The present process will therefore now be more particularly described with reference to this preferred embodiment.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

The cyclohexene can be supplied to the reaction zone as a separate feed from the benzene, but normally is produced in situ by selective hydrogenation of the benzene in the presence of a hydrogenation component on the catalyst that has an alkylation function. The bifunctional catalyst is therefore referred to herein as a hydroalkylation catalyst and overall the hydroalkylation reaction proceeds as follows to produce cyclohexylbenzene (CHB):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4:1 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 hr$^{-1}$ to about 10 hr$^{-1}$ on total feed, and a benzene/dicyclohexylbenzene weight ratio of about 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminphosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components comprise at least one metal selected from Groups 6 to 10 of the Periodic Table of Elements, such as platinum, palladium and compounds, and mixtures thereof. Typically, the hydrogenation-dehydrogenation component is present in an amount between about 0.1 wt % and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 wt % and about 5 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing compound, such as air and various derivatives of air.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1- hydroperoxide based upon the total weight of the oxidation reaction effluent. The oxidation reaction effluent may further comprise unreacted imide catalyst and unreacted cyclohexylbenzene. As used herein, "unreacted imide catalyst" and "unreacted cyclohexylbenzene" mean imide catalyst and cyclohexylbenzene respectively that were not consumed or otherwise transformed in the oxidation reaction. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is then subjected to a cleavage reaction, either directly or after undergoing prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide, and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3 A molecular sieve, to separate water and other absorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939, the entire contents of which are incorporated herein by reference.

In another embodiment, all or a fraction of the oxidation effluent may be contacted with an aluminosilicate zeolite of the FAU type to reduce the amount of unreacted imide catalyst (i.e., the cyclic imide catalyst that does not react in the oxidation reaction) in the effluent by adsorption onto the zeolite. The FAU type zeolite employed to remove the oxidation catalyst may be same as the FAU type zeolite employed in the cleavage reaction, namely having a unit cell size less than 24.35 Å, such as less than 24.30 Å, and the contacting to remove the oxidation catalyst can be conducted prior to or concurrently with the cleavage reaction. The adsorbed imide catalyst can be desorbed from the FAU type zeolite by washing with a polar solvent, such as acetone or cyclohexanone, and recovered by flashing off the solvent and/or by recrystallization. The recovered imide can then be recycled to the oxidation reaction.

In general, however, the need for removal of unreacted cyclic imide catalyst from the oxidation effluent is obviated, or at least reduced, in the present process by the selection of a molecular sieve catalyst for the cleavage step. In another embodiment, the unreacted cyclic imide catalyst is not deliberately removed from the product prior to the cleavage step. As used herein, "not deliberately removed" means that no steps were undertaken for the purpose of removing the unreacted cyclic imide from the oxidation effluent. In another embodiment, less than 5 wt %, or less than 10 wt %, or less than 20 wt %, or less than 35 wt %, or less than 50 wt %, or less than 60 wt %, or less than 70 wt % or less than 80 wt % of the unreacted cyclic imide catalyst is removed from the oxidation effluent prior to the cleavage step, the wt % s based upon the total weight of the oxidation effluent.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

The acid catalyst used in the present cleavage reaction is a molecular sieve (e.g., an acidic molecular sieve) and in particular, a molecular sieve having a pore size in excess of 7 Å. Examples of suitable molecular sieves include zeolite beta, zeolite Y, zeolite X, ZSM-12, and mordenite. In one embodiment, the molecular sieve is a FAU-type zeolite. As used herein, "FAU-type zeolite" or "zeolite of the FAU type" means a zeolite having a FAU-type structure as described in the *Atlas of Zeolite Framework Types*, Ch. Baerlocher et al. (6th Ed. 2007). "FAU-type" catalysts include faujasite. The zeolite can be used in unbound form or can be combined with a binder, such as silica or alumina, such that the overall catalyst (zeolite plus binder) comprises from about 20 wt % to about 80 wt % of the zeolite. In one embodiment, the molecular sieve comprises a FAU type zeolite having a unit cell size less than 24.35 Å, such as less than or equal to 24.30 Å, even less than or equal to 24.25 Å. Unit cell size is determined by X-ray diffraction as described in ASTM D-3942.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The cleavage reaction can be conducted in a variety of reactor configurations and in either a single reactor or in a plurality of reactors. For example, the reaction may be conducted at least a first reactor and a second reactor connected in series, with the first reactor being operated at a temperature of about 20° C. to about 120° C. and a pressure of about 100 kPa to about 500 kPa, and the second reactor being operated at a temperature of about 40° C. to about 180° C. and a pressure of about 100 kPa to about 1000 kPa. The first and second reactors may be the same or different.

In one embodiment, at least part of the cleavage reaction is conducted in a continuous stirred tank reactor (CSTR), with the catalyst being slurried in the cleavage reaction medium. Typically, the catalyst is added in an amount between about 50 wppm and about 20,000 wppm of the cleavage reaction medium. Advantages for this configuration include easy heat management and flexibility to add/withdraw catalyst to maintain conversion as the catalyst deactivates. Since peroxide cleavage is performed with the oxidation product containing at least part of the imide catalyst, the latter will adsorb on the catalyst, gradually inhibiting its performance. However, the imide catalyst adsorbed on the catalyst can readily be removed and recovered by washing the spent catalyst with a polar solvent such as acetone or cyclohexanone. In this way, the catalyst recovers its cleavage activity and imide adsorbing capacity, while the desorbed imide catalyst can be separated from the polar solvent and recycled to the oxidation step. The deactivated catalyst can be also regenerated by burning off coke in air, although such air-regeneration is advantageously performed after desorbing the imide from the catalyst. In a slurry cleavage process, the catalyst can be regenerated on various schedules. Advantageously, the catalyst would be continuously withdrawn from the cleavage reactor, regenerated in an external recycle loop, and then returned into the cleavage reactor. Under such operation regime, a steady state of catalyst activity can be maintained through regeneration and by continuously replacing a fraction of the recycled catalyst with fresh catalyst.

The FAU catalyst can also be used in a fixed bed plug-flow reactor. In such a process design, two or more parallel cleavage reactor trains may be deployed to enable uninterrupted processing of the peroxide feed. Thus, as the FAU catalyst is saturated with the imide catalyst causing it to deactivate in one reactor train, the cleavage feed is switched to another reactor train that contains fresh or regenerated catalyst. The imide-saturated catalyst can be rejuvenated off-line by, for example, flushing with a polar solvent such as acetone or cyclohexanone. The imide catalyst recovered can be re-used for oxidation. The coke on catalyst can then also be removed by burning in air before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

The major products of the cleavage reaction are phenol and cyclohexanone, each of which generally comprises about 40 wt % to about 60 wt %, or about 45 wt % to about 55 wt % of the cleavage reaction product, such wt % based on the weight of the cleavage reaction product exclusive of unreacted cyclohexylbenzene and acid catalyst.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the following non-limiting examples and the accompanying drawings.

Example 1

Oxidation of Cyclohexylbenzene

An amount of 631 g of cyclohexylbenzene (CHB, TCI America, Inc.) was added to a 1-liter four-necked glass flask, to which 0.6702 g of NHPI (TCI America, Inc.) was added. The flask was then fitted with a reflux condenser, a mechanical stirrer, a gas sparger, and a thermometer. An air flow of 250 cc/min was bubbled through the liquid via the gas sparger; and the contents of the flask were heated at 110° C. with stirring (560 rpm) for 6 hours. The flask was allowed to cool down to room temperature and the oxidation product recovered. GC analysis indicated the product contains 17.9% CHBHP. The oxidation product also contained about 1060 ppm of NHPI.

Example 2

Removal of NHPI

An amount of 300 g of the oxidation products from Example 1 was placed in a 500-mL glass flask and mixed with 30 g of anhydrous sodium carbonate (granular form, Aldrich). The mixture was stirred overnight and the solid became brick-red in color. The solid was then removed by filtration and the liquid further filtered through a bed of anhydrous magnesium sulfate. A clear, light-yellow liquid was obtained. GC analysis revealed the product to contain 17.5% CHBHP and <10 ppm NHPI.

Example 3

Cleavage of CHBHP (~3 wt % CHBHP) Using Faujasite in Batch Operation

An amount of 30 g mixture of CHBHP/CHB/phenol/cyclohexanone (about 3/81/8/8 wt. ratio) and dodecane (internal standard) was charged to a 50-cc jacketed glass reactor with a circulating temperature bath. The bath was set to desired temperature and the reactor contents were allowed to equilibrate. Once the temperature stabilized, a GC sample was taken for the hot feed. The desired amount of a faujasite catalyst commercially available from Zeolyst International under the trade name CBV760 (with a silica to alumina molar ratio of 60 and a unit cell size of 24.24 Å) was then added to the mixture. A brief reaction exotherm was noted, as indicated by the temperature rise inside the reactor, and after a 15 minute interval a 1-cc aliquot was removed from the reactor and the solid filtered. The samples generated were analyzed by GC and the results are summarized in Table 1.

TABLE 1

| Catalyst (Si/Al$_2$) | Catalyst loading | NHPI in feed (ppm) | CHBHP conv. (%) | Phenol selectivity (%) | Cyclohexanone selectivity (%) |
|---|---|---|---|---|---|
| CBV760 | 2% | <10 | 99 | 96 | 93 |
| CBV760 | 2% | ~180 | 99 | 98 | 93 |
| CBV760 | 1% | ~180 | 98 | 98 | 93 |

The results shown in Table 1 demonstrate that the presence of NHPI did not affect the selectivity of the cleavage catalyzed by the faujasite catalyst. As used herein, "CHBHP conversion" means the amount of cyclohexylbenzene hydroperoxide converted to any product. "Phenol selectivity" is relative to the theoretical phenol yield based upon the amount of cyclohexylbenzene hydroperoxide converted. "Cyclohexanone selectivity" is relative to the theoretical cyclohexanone yield based upon the amount of cyclohexylbenzene hydroperoxide converted. "Catalyst loading" means the amount of cleavage catalyst per unit amount of the cleavage feed mixture.

Example 4

Concurrent CHBHP Cleavage and NHPI Removal Using Faujasite in a Packed Column

A glass column with a stop-cock was packed with glass wool and 10 g of 1 mm glass beads, on top of which was packed 1 g of faujasite powder CBV760, commercially available from Zeolyst International (having a silica to alumina molar ratio of 60 and a unit cell size of 24.24 Å). A volume of 5 cc CHB oxidation mixture containing 22 wt % CHBHP and 550 ppm NHPI (referred as the stock solution) was added to the column and allowed to contact and travel through the bed over a period of 60 min. The liquid was collected and both the CHBHP the NHPI levels were analyzed. Repeatedly, 5 cc of the stock solution was added and the liquid collected was analyzed. CHBHP conversion and the level of NHPI are plotted against the number of contact cycles in FIG. 1.

The process was repeated but using faujasite powder CBV780, also commercially available from Zeolyst International (having a silica to alumina molar ratio of 80 and a unit cell size of 24.24 Å) as the cleavage catalyst. The results are shown in FIG. 2.

Figure 1:
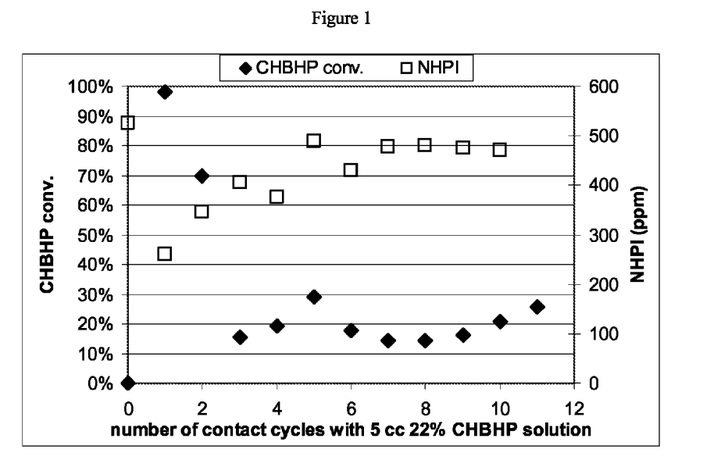
FIG. 1 is a graph of weight % conversion of cyclohexylbenzene hydroperoxide and level of NHPI against number of cleavage cycles in the process of Example 4 using faujasite CBV760 as the cleavage catalyst.
Figure 2:
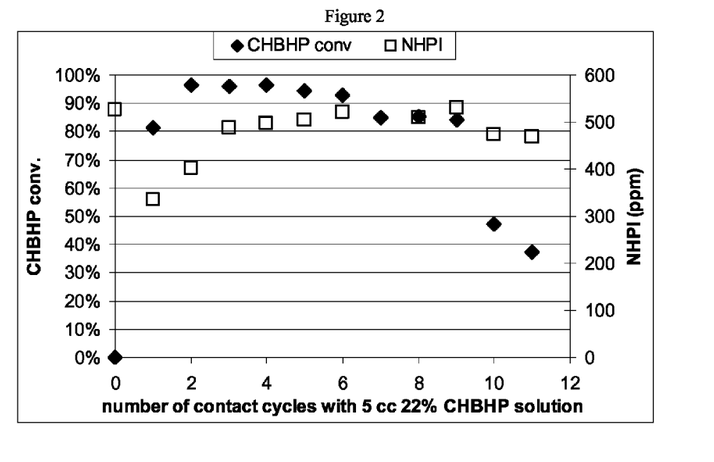
FIG. 2 is a graph of weight % conversion of cyclohexylbenzene hydroperoxide and level of NHPI against number of cleavage cycles in the process of Example 4 using faujasite CBV780 as the cleavage catalyst.

From FIGS. 1 and 2, it can be seen CBV780 showed higher CHBHP cleavage activity but lower NHPI absorption capacity (0.31 wt %); whereas CBV760 shows higher NHPI absorption capacity (0.63 wt %) but lower activity for CHBHP cleavage.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol, the process comprising:
   (a) contacting cyclohexylbenzene with an oxygen-containing compound in the presence of an oxidation catalyst comprising a cyclic imide under oxidation conditions effective to produce a product comprising cyclohexylbenzene hydroperoxide and unreacted cyclic imide catalyst; and
   (b) contacting at least a portion of the product with an acidic molecular sieve comprising an aluminosilicate FAU-type zeolite having unit cell size less than 24.35 Å under conditions effective to adsorb at least a portion of the unreacted cyclic imide and convert at least a portion of the cyclohexylbenzene hydroperoxide in said product into phenol and cyclohexanone, wherein less than 50 wt % of the unreacted cyclic imide catalyst is removed from the product prior to the contacting step (b).

2. The process of claim 1, wherein the unreacted cyclic imide catalyst is not deliberately removed from the product prior to the contacting step (b).

3. The process of claim 1, wherein less than 20 wt % of the unreacted cyclic imide is removed from the product prior to the contacting step (b).

4. The process of claim 1, wherein less than 5 wt % of the unreacted cyclic imide is removed from the product prior to the contacting step (b).

5. The process of claim 1, wherein said aluminosilicate FAU-type zeolite has a pore size greater than 7 Å.

6. The process of claim 1, wherein said FAU type zeolite has a unit cell size less than or equal to 24.30 Å.

7. The process of claim 1, wherein the cyclic imide catalyst is N-hydroxyphthalimide.

8. The process of claim 1, wherein said conditions in the contacting step (b) include a temperature of about 20° C. to about 200° C. and a pressure of about 100 kPa to about 2000 kPa.

9. The process of claim 1, wherein the contacting step (b) is conducted in at least a first reactor and a second reactor connected in series.

10. The process of claim 9, wherein the first reactor is operated at a temperature of about 20° C. to about 120° C. and a pressure of about 100 kPa to about 500 kPa, and the second reactor is operated at a temperature of about 40° C. to about 180° C. and a pressure of about 100 kPa to about 1000 kPa.

11. The process of claim 1, wherein the contacting step (b) is conducted in at least one of a plurality of reactors connected in parallel.

12. The process of claim 11, wherein the acidic molecular sieve is regenerated in a first reactor during operation of the contacting step (b) in a second reactor.

13. The process of claim 12, wherein acidic molecular sieve regeneration comprises flushing the acidic molecular sieve with a polar organic solvent to remove at least part of the cyclic imide adsorbed on the acidic molecular sieve.

14. The process of claim 1, wherein the contacting step (b) is at least partly conducted in a continuously stirred tank reactor.

15. The process of claim 12, wherein the regenerated acidic molecular sieve is returned to the contacting step (b).

16. The process of claim 1, wherein the acidic molecular sieve is continuously or periodically added to the contacting step (b) to maintain conversion.

17. The process of claim 1, wherein the contacting step (b) is at least partly conducted in a fixed bed reactor.

18. The process of claim 1, wherein at least a portion of the phenol is converted to at least one of a phenolic resin, bisphenol A, ∈-caprolactam, an adipic acid, or a plasticizer.

19. The process of claim 1, wherein at least a portion of the cyclohexanone is converted into at least one of adipic acid, a cyclohexanone resin, a cyclohexanone oxime, caprolactam, or nylon.

20. A process for producing phenol, the process comprising:
- (a) contacting cyclohexylbenzene with an oxygen-containing compound in the presence of an oxidation catalyst comprising a cyclic imide under oxidation conditions effective to produce a product comprising cyclohexylbenzene hydroperoxide and unreacted cyclic imide catalyst; and
- (b) contacting at least a portion of the product containing cyclohexylbenzene hydroperoxide and at least 50 ppmw of the unreacted cyclic imide catalyst with an acidic molecular sieve comprising an aluminosilicate FAU-type zeolite having unit cell size less than 24.35 Å under conditions effective to adsorb at least a portion of the unreacted cyclic imide and to convert at least a portion of the cyclohexylbenzene hydroperoxide in said product portion into phenol and cyclohexanone.

21. The process of claim 20, wherein at least a portion of the cyclic imide catalyst is desorbed from said acidic molecular sieve and recycled to said contacting step (a).

22. A process for producing phenol, the process comprising:
- (a) hydroalkylating benzene with hydrogen in the presence of a hydroalkylation catalyst under conditions effective to produce a hydroalkylation reaction product comprising cyclohexylbenzene;
- (b) separating cyclohexylbenzene from said hydroalkylation reaction product;
- (c) contacting at least a portion of said cyclohexylbenzene from said separating step (b) with an oxygen-containing compound in the presence of an oxidation catalyst comprising a cyclic imide under oxidation conditions effective to produce a cleavage product comprising cyclohexylbenzene hydroperoxide and unreacted cyclic imide catalyst; and
- (d) contacting at least a portion of the product with an acidic molecular sieve comprising an aluminosilicate FAU-type zeolite having unit cell size less than 24.35 Å under conditions effective to adsorb at least part of the cyclic imide and to convert at least part of the cyclohexylbenzene hydroperoxide in said product portion into phenol and cyclohexanone, wherein less than 50 wt % of the unreacted cyclic imide catalyst is removed from the product prior to the contacting step (d).

\* \* \* \* \*